United States Patent [19]

Miki et al.

[11] Patent Number: 4,797,274

[45] Date of Patent: Jan. 10, 1989

[54] COMPOSITION COMPRISING COPPER COMPOUND

[75] Inventors: Yoshiaki Miki, Yokohama; Tsunehisa Ueda, Zushi, both of Japan

[73] Assignee: Nippon Zeon Co., Ltd., Tokyo, Japan

[21] Appl. No.: 89,178

[22] Filed: Aug. 25, 1987

[30] Foreign Application Priority Data

Aug. 26, 1986 [JP] Japan .................................. 61-199568

[51] Int. Cl.$^4$ ..................... A01N 37/42; A01N 59/20; A61L 9/01
[52] U.S. Cl. .................................... 424/76.1; 424/141
[58] Field of Search ....................... 424/140, 141, 76.1

[56] References Cited

U.S. PATENT DOCUMENTS

| | | | |
|---|---|---|---|
| 2,337,466 | 12/1943 | Herbert | 424/141 |
| 2,359,413 | 10/1944 | Freedman | 424/141 X |
| 2,362,760 | 11/1944 | Maxwell | 424/141 X |
| 2,777,791 | 1/1957 | Visor et al. | 424/141 |
| 2,798,023 | 7/1957 | Berger | 424/141 X |
| 3,094,459 | 6/1963 | Pickren | 424/141 |
| 3,681,492 | 8/1972 | Kotzbauer | 424/141 |
| 3,961,933 | 6/1976 | Kuyama et al. | 424/141 X |
| 4,110,467 | 8/1978 | Sano et al. | 424/141 X |

FOREIGN PATENT DOCUMENTS 6341408 8/1986 Japan .

*Primary Examiner*—Nancy A. B. Swisher
*Attorney, Agent, or Firm*—Sherman and Shalloway

[57] ABSTRACT

A composition comprising a copper compound, and blended with it, (A) an L-ascorbic acid compound and/or an erythorbic acid compound and (B) a hydroxycarboxylic acid compound. The compound has excellent deodorizing, fungicidal and moldproof properties.

15 Claims, No Drawings

COMPOSITION COMPRISING COPPER COMPOUND

This invention relates to a novel composition comprising a copper compound. More specifically, it relates to a novel composition having excellent deodorizing, fungicidal and moldproof properties comprising a copper compound, and blended with it, (A) an L-ascorbic acid compound and/or an erythorbic acid compound, (B) a hydroxycarboxylic acid compound and as required, water.

Copper sulfate, copper chloride and other various copper compounds are utilized as raw materials in a variety of applications, for example for the production of deodorants, fungicides, insecticides, agricultural chemicals, pharmaceuticals and catalysts. In particular, they are known to have excellent deodorizing and fungicidal properties. Generally, however, these copper compounds are difficult to use because they form precipitates with deodorizing alkaline substances such as ammonia. Furthermore, many of them are toxic and cannot be used alone in large amounts. Hence, these copper compounds have the defect of finding only limited utility from the standpoint of safety and performance.

The present inventors previously found that the combined use of the copper compounds with hydroxycarboxylic acid compounds can inhibit formation of precipitates during deodorization of alkaline substances. The hydroxycarboxylic acid compounds have been used in various applications as, for example, pharmaceuticals, food additives, deodorants and stabilizers by utilizing their acid component and their chelating and other functions. The combination of a copper compound and a hydroxycarboxylic acid compound can inhibit formation of precipitates. But the two compounds form a chelate which inhibits the deodorizing ability of the copper compound. It is necessary therefore to increase the amount of the copper compound markedly.

The present inventors have made extensive investigations in order to eliminate these defects of the prior art, and have found that a composition comprising a copper compound, and blended with it, (A) an L-ascorbic acid compound and/or an erythorbic acid compound, (B) a hydroxycarboxylic acid compound, and as required, water can inhibit formation of a precipitate without impairing the function of the copper compound. This finding has led to the present invention.

Thus, according to this invention, there is provided a composition comprising a copper compound, and blended with it (A) an L-ascorbic acid compound and/or an erythorbic acid compound, (B) a hydroxycarboxylic acid compound, and as required, water.

The copper compound used in this invention may be any of those compounds which contain copper, for example, inorganic acid salts, organic acid salts, complexes and oxides of copper. Specific examples include copper sulfate, copper nitrate, cuprous chloride, cupric chloride, cuprous bromide, cupric bromide, cuprous iodide, copper carbonate, cupric hydroxide, cupric sulfide, copper cyanide, copper acetate, cupric citrate, copper gluconate, copper malate, copper pyrophosphate, copper chlorophyll, copper chlorophyllin sodium, copper phthalocyanine, copper porphyrin, cuprous oxide and cupric oxide. Among them, the inorganic acid salts are preferred from the viewpoint of cost and availability, and the complexes are preferred because of safety.

It should be understood that when the copper compound is copper L-ascorbate, copper erythorbate or a copper hydroxycarboxylate, the composition of this invention contains the copper compound and component (A) or (B) without separately adding the component (A) or (B).

The L-ascorbic acid compound and erythorbic acid compound as component (A) are known as antioxidants for foods. These compounds may be used in acid form and in the form of water-soluble salts as well. In the present invention, the L-ascorbic acid compound and erythorbic acid compound may be used singly or in combination.

The hydroxycarboxylic acid compound as component (B) is a hydroxycarboxylic acid containing at least one hydroxyl group and at least one carboxyl group in the molecule, or its water-soluble salt. Specific examples include aliphatic or aromatic compounds such as lactic acid, hydroxyacetic acid, hydroxybutyric acid, malic acid, tartaric acid, glyceric acid, citric acid, alphamethylmalic acid, beta-hydroxyglutaric acid, desoxalic acid, monoethyl tartrate, monoethyl citrate, gluconic acid, galactaric acid, glucuronic acid, ketogluconic acid, salicylic acid, p-hydroxybenzoic acid, gallic acid and hydroxyphthalic acid; and water-soluble salts (e.g., sodium, potassium or ammonium salts) of these compounds. Of these, the aliphatic compounds are preferred.

The amounts of the individual compounds may be properly chosen according to the properties required of the final composition of this invention. The amount of the L-ascorbic acid compound and/or erythorbic acid compound blended is usually 0.01 to 100 moles, preferably 0.05 to 50 moles, per mole of the copper ion in the copper compound. If the amount is excessively small, the function of the resulting composition might become insufficient. Excessively large amounts are sometimes uneconomical. The amount of the hydroxycarboxylic acid blended is usually 0.1 to 1000 moles, preferably 0.5 to 250 moles, per mole of the copper ion in the copper compound.

As required, the composition of this invention may be used in combination with conventional deodorants, fungicides and moldproof agents, or various additives such as pigments, coloring agents, stabilizers and antioxidants may be added to the composition, so long as these additional agents do not impair the functions of the composition of the invention.

There is no particular restriction on the method by which the composition of this invention is prepared. For example, the individual components are uniformly dissolved in water to form the composition as an aqueous solution. The aqueous solution may be dried by, for example, lyophilization or spray drying to obtain the composition as a dry mixture. Alternatively, crystalline powders of the individual components may be uniformly mixed to obtain the composition as a dry mixture.

The form of the composition is neither restricted in particular. It may, for example, be in the form of an aqueous solution, a powder or a tablet. As required, the aqueous solution may be impregnated or coated in or on an impregnatable or coatable substrate such as paper, cloths, foamed sheets, pulp, and fibers. It may also be supported on a carrier such as bentonite, activated carbon and zeolite. The amount of the composition based on the substrate or carrier is not particularly restricted, and may vary according to the use to which it is put and the method of using it. Usually, it is 10 to 20% by weight as solids. If the amount of the composition is excessively small, its function might be insufficient. Excessively large amounts are sometimes uneconomical.

The composition of this invention obtained as above is useful as a deodorant, a fungicide or a moldproof agent.

Thus, the present invention can give a novel composition which can inhibit formation of a precipitate at the time of using the copper compound singly and can be used without impairing the deodorizing function of the copper compound.

The following Examples and Comparative Examples illustrate the present invention more specifically. In all these examples, parts and percentages are by weight unless otherwise specified.

In each run, copper sulfate ($CuSO_4.5H_2O$), L-ascorbic acid and hydroxycarboxylic acid in the amounts indicated in Table 1 were dissolved in distilled water to prepare 10 g of an aqueous solution.

Fifty milligrams of the resulting aqueous solution was put in a 100 ml Erlenmeyer flask, and the flask was stopped. One milliliter of ethylmercaptan (0.5 g/3 liter $N_2$) was added. Ethylmercaptan in the vapor phase was periodically quantified by gas chromatography, and the ratio of decrease of ethylmercaptan (as a measure of mercaptan deodorizing ability) was calculated. The results are shown in Table 1.

Separately, 100 mg of the aqueous solution was put in a 100 ml Erlenmeyer flask, and the flask was stopped. Then, 50 microliters of a 28% aqueous solution of ammonia was added, and ammonia in the vapor phase was periodically quantified by gas chromatography, and the ratio of decrease of ammonia (a measure of ammonia deodorizing ability) was calculated. Ten minutes after deodorizing ammonia, the appearance of the solution was observed. The results are also shown in Table 1.

TABLE 1

| Run No. | Copper Sulfate (mg) | L-ascorbic acid or erythorbic acid (*1) (mg) | Mole ratio (*2) | Hydroxycarboxylic acid Citric acid (mg) | Gluconic acid (mg) | Mole ratio (*3) | Decrease ratio (%) of ethylmercaptan 5 min. later | 10 min. later | 30 min. later | Decrease ratio (%) of ammonia 1 min. later | 5 min. later | 10 min. later | Appearance observed 10 min. after ammonia deodorization |
|---|---|---|---|---|---|---|---|---|---|---|---|---|---|
| Example | | | | | | | | | | | | | |
| 1-1 | 10 | 100 | 14 | 10 | — | 1.2 | 74 | 97 | 100 | 51 | 82 | 98 | Green, transparent |
| 1-2 | 10 | 100 | 14 | 100 | — | 12 | 76 | 95 | 100 | 65 | 93 | 100 | Green, transparent |
| 1-3 | 10 | 100 | 14 | 1000 | — | 120 | 74 | 97 | 100 | 78 | 96 | 100 | Green, transparent |
| 1-4 | 10 | 10 | 1.4 | 100 | — | 12 | 69 | 86 | 99 | 75 | 91 | 100 | Green, transparent |
| 1-5 | 10 | 100 | 14 | — | 100 | 13 | 71 | 90 | 100 | 86 | 98 | 100 | Green, transparent |
| 1-6 | 10 | 100 | 14 | 1000 | — | 120 | 67 | 92 | 100 | 81 | 94 | 100 | Green, transparent |
| Comparative Example | | | | | | | | | | | | | |
| 2-1 | 10 | — | — | 10 | — | 1.2 | 34 | 53 | 78 | 49 | 77 | 96 | Blue, transparent |
| 2-2 | 10 | — | — | 100 | — | 12 | 19 | 42 | 71 | 66 | 90 | 100 | Blue, transparent |
| 2-3 | 10 | — | — | 1000 | — | 120 | 18 | 32 | 58 | 85 | 96 | 100 | Blue, transparent |
| 2-4 | 10 | — | — | — | 100 | 13 | 13 | 30 | 49 | 71 | 92 | 100 | Blue, transparent |
| 2-5 | 10 | — | — | — | — | — | 78 | 96 | 100 | 63 | 91 | 99 | Precipitate formed |

(*1): In Run No. 1-6 alone, erythorbic acid was used.
(*2): Moles of L-ascorbic acid or erythorbic acid per mole of the copper ion in coper sulfate.
(*3): Moles of the hydroxycarboxylic acid per mole of the copper ion in the copper compound.

Table 1 shows that the compositions in accordance with this invention can inhibit formation of precipitates at the time of deodorizing ammonia, and have better deodorizing ability than the combination of a copper compound and a hydroxycarboxylic acid.

What is claimed is:

1. A composition comprising a copper compound, and blended with it, (A) an L-ascorbic acid compound and/or an erythorbic acid compound and (B) an hydroxycarboxylic acid compound.

2. The composition of claim 1 which is in the form of an aqueous solution.

3. The composition of claim 1 which is in the form of a powder.

4. The composition of claim 3 which is obtained by drying the aqueous solution of claim 2.

5. The composition of claim 3 which is obtained by blending a powder of the copper compound with components (A) and (B).

6. The composition of claim 1 wherein the amount of component (A) blended is 0.01 to 100 moles per mole of the copper ion in the copper compound.

7. The composition of claim 1 wherein the amount of component (B) blended is 0.1 to 1000 moles per mole of the copper ion in the copper compound.

8. The composition of claim 1 wherein the copper compound is copper sulfate, cupric chloride or copper chlorophyllin sodium.

9. The composition of claim 1 wherein the hydroxycarboxylic acid compound is an aliphatic hydroxycarboxylic acid compound.

10. The composition of claim 1 wherein the hydroxycarboxylic acid compound is a compound having 2 to 8 carbon atoms.

11. The composition of claim 1 wherein the hydroxycarboxylic acid is citric acid or gluconic acid.

12. A composition capable of deodorizing alkaline substances including ammonia and mercaptan which comprises a copper compound selected from the group consisting of inorganic acid salts, organic acid salts, complexes and oxides of copper, with (A) 0.01 to 100 moles, per mole of the copper ion in the copper compound, of L-ascorbic acid, erythorbic acid, or mixtures thereof, and (B) from 0.1 to 1,000 moles, per mole of the copper ion in the copper compound of a hydroxycarboxylic acid or a water-soluble salt thereof whereby when used in the deodorization of alkaline substances, such as ammonia, precipitation of the copper compound is inhibited and whereby the formation of a chelate of the copper compound with the hydroxycarboxylic acid compound is also inhibited.

13. The composition of claim 12 wherein the amount of component (A) is from 0.05 to 50 moles, per mole of the copper ion in the copper compound, and the amount of the component (B) is from 0.5 to 250 moles, per mole of the copper ion in the copper compound.

14. The composition of claim 12 wherein the copper compound is copper sulfate, cooper chloride or copper chlorophyllin sodium, and component (A) is an aliphatic hydroxycarboxylic acid having 2 to 8 carbon atoms.

15. The composition of claim 14 wherein the hydroxycarboxylic acid is citric acid or gluconic acid.

* * * * *